United States Patent
Rodriguez

(10) Patent No.: US 6,517,023 B2
(45) Date of Patent: Feb. 11, 2003

(54) BANDAGE APPLICATOR

(76) Inventor: José Luis Corrales Rodriguez, Urb. La Ribera, 39. Casa Concordia, 18690 Almuñécar, Granada (ES)

( * ) Notice: Subject to any disclaimer, the term of this patent is extended or adjusted under 35 U.S.C. 154(b) by 0 days.

(21) Appl. No.: 09/883,267

(22) Filed: Jun. 19, 2001

(65) Prior Publication Data

US 2002/0063183 A1 May 30, 2002

(30) Foreign Application Priority Data

Nov. 27, 2000 (ES) .................................. U-200002903

(51) Int. Cl.⁷ .......................... B65H 23/06; B65H 16/04
(52) U.S. Cl. ................. 242/422.4; 242/588.2; 242/597.6; 242/609.1; 242/611.2
(58) Field of Search .................. 242/422.4, 396.8, 242/588.2, 609.1, 611.2, 597.6; 128/851

(56) References Cited

U.S. PATENT DOCUMENTS

| | | | | |
|---|---|---|---|---|
| 3,198,175 A | * | 8/1965 | Dean ....................... | 242/396.8 |
| 3,556,426 A | * | 1/1971 | Olander ................... | 242/609.1 |
| 3,770,221 A | * | 11/1973 | Stern ........................ | 242/422.4 |
| 4,248,392 A | | 2/1981 | Parry | |
| 4,484,717 A | | 11/1984 | Goldstein | |
| 4,714,211 A | | 12/1987 | Hwang | |
| 4,722,493 A | | 2/1988 | Parry et al. | |
| 4,784,348 A | | 11/1988 | McDonald | |
| 4,817,762 A | | 4/1989 | Powell | |
| 4,934,312 A | | 5/1989 | Riemenshneider, III | |
| 4,872,623 A | | 10/1989 | Parry et al. | |
| 4,880,181 A | * | 11/1989 | Drahanowsky .......... | 242/611.2 |
| 5,203,517 A | | 4/1993 | Parry et al. | |
| 5,257,749 A | * | 11/1993 | Liepold et al. .......... | 242/611.2 |
| 5,351,905 A | | 10/1994 | Ferber ..................... | 242/588.2 |
| 5,524,843 A | | 6/1996 | McCauley ............... | 242/532.6 |
| 5,664,739 A | | 9/1997 | Black et al. ............. | 242/588.5 |
| 5,927,635 A | | 7/1999 | Black et al. ................ | 242/395 |
| 6,102,323 A | | 4/2000 | Riemenschneider ..... | 242/422.4 |
| 6,286,779 B1 | | 9/2001 | Devine ........................ | 242/532 |

FOREIGN PATENT DOCUMENTS

| | | |
|---|---|---|
| GB | 2203726 A | 10/1988 |
| GB | 2333506 A | 7/1999 |
| GB | 2299321 A | 10/2000 |

* cited by examiner

Primary Examiner—John M. Jillions
(74) Attorney, Agent, or Firm—Law Offices of David G. Posz; Kerry S. Culpepper

(57) ABSTRACT

The present invention relates to a sheet material applicator comprising a cylindrical body rotatable within a housing, the housing forming a handle for the applicator, and means at one end of the cylindrical body for mounting a roll of the sheet material particularly a bandage applicator.

4 Claims, 3 Drawing Sheets

BANDAGE APPLICATOR

The present invention relates to an applicator for a sheet material, particularly to a bandage applicator allowing the comfortable and precise placement of the bandage by a person alone.

At the present time, bandages are applied by hand, thus making it necessary to unroll the bandage with the fingers as the bandage roll is passed around the area to be protected.

This is inconvenient and inappropriate, particularly in the application of bandages by the patient, especially when there is a deficiency in dexterity of the fingers, with the additional problem that, even in the case of experienced personnel, it is difficult to achieve a homogeneous level of tension in the bandage.

According to the present invention, there is provided a sheet material applicator comprising a cylindrical body rotatable within a housing, the housing forming a handle for the applicator, and means at one end of the cylindrical body for mounting a roll of the sheet material.

In a preferred embodiment, the sheet material applicator is a bandage applicator.

The bandage applicator in the present invention alleviates the problems described in a simple manner as it allows the bandage to be applied, even by the patient himself or herself, quickly, easily and flexibly, without requiring the bandage to be unrolled with the fingers while the bandage is being applied. In addition, it has certain devices to ensure the optimal regulation of the tension in the unwinding of the bandage.

In accordance with the present invention, the applicator comprises a main cylindrical body, preferably open at one of its ends, presenting two peripheral projections and certain means for attachment, at its non-open end, intended for the placement of a tubular part. On the periphery of the latter, the end of the bandage is attached and the bandage is wound around the tubular part. The said part may be made of a single segment or in various segments.

The tubular part may be placed by inserting it through either end of the applicator, thus making it possible for the same to turn and the bandage to be unwound under the most favorable circumstances, even if the user changes hands or the direction in which the bandage is unwinding.

The means of attachment mentioned above are made in such a way as to make the movement of the main part and the tubular part interlocked and turning at the same time. The said means of attachment are preferably made from a cylindrical portion sticking out from the main part at its non-open end, into which some longitudinal slots are made on the sides, intended for the insertion by means of grooving and tonguing of certain internal ridges present on the inside of the tubular part.

On one of the projections of the main body, two half-casings are inserted by means of grooving and tonguing to act as the handle of the applicator, so that by holding the same by means of the handle it is possible for the main body and the tubular part to turn and for the bandage to unwind.

The other projection comprises a braking area for stopping the movement of the bandage as it unwinds, preventing or slowing down this movement by means of pressure on this area with a finger or any other mechanical element, preferably presenting this are certain small studs so as to enhance this braking function.

The invention will now be more particularly described with reference to the drawings in which.

Figure 1:
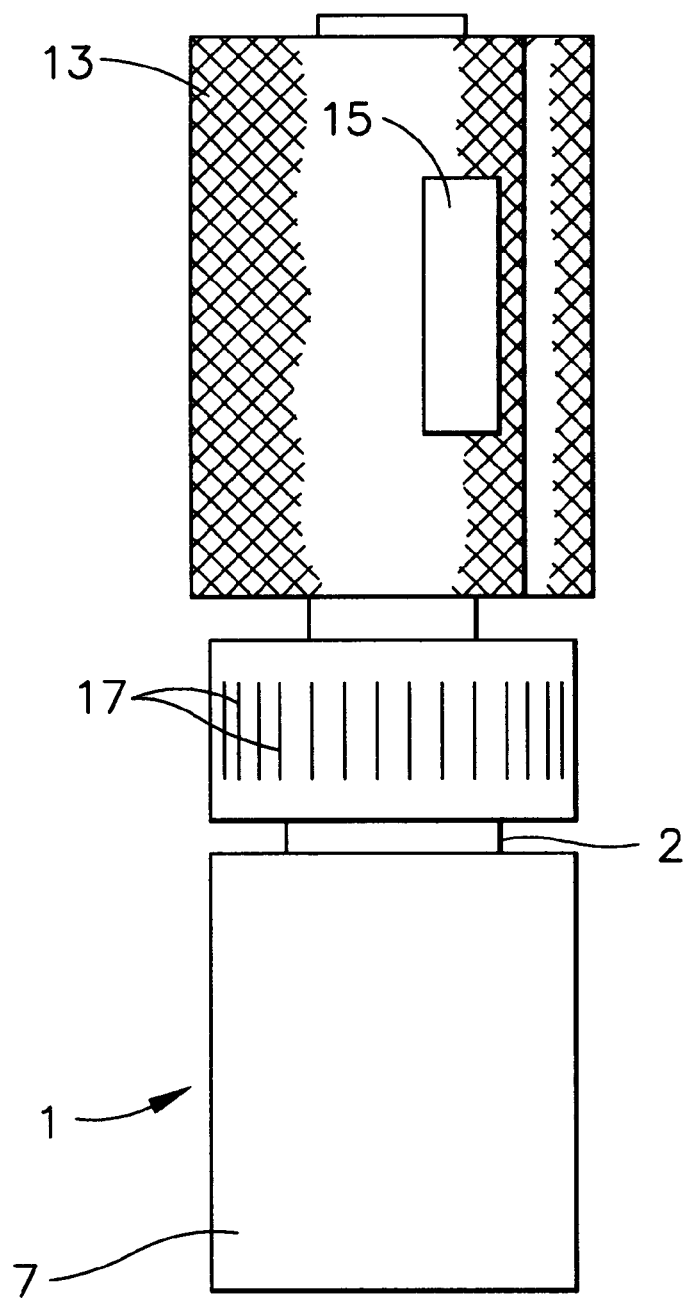
FIG. 1 shows a side view of the bandage applicator included in the present invention.
Figure 2:
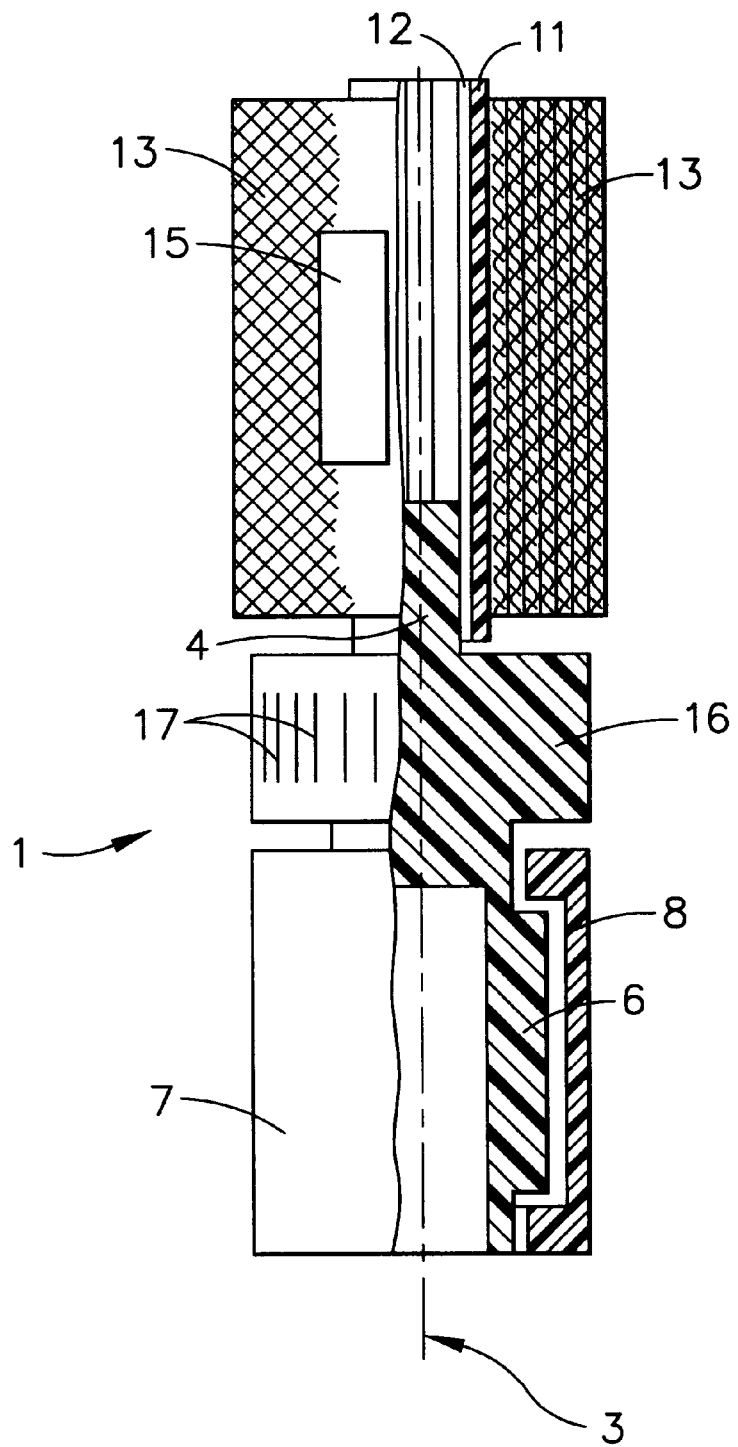
FIG. 2 shows a one-quarter cutaway drawing of FIG. 1.
Figure 3:
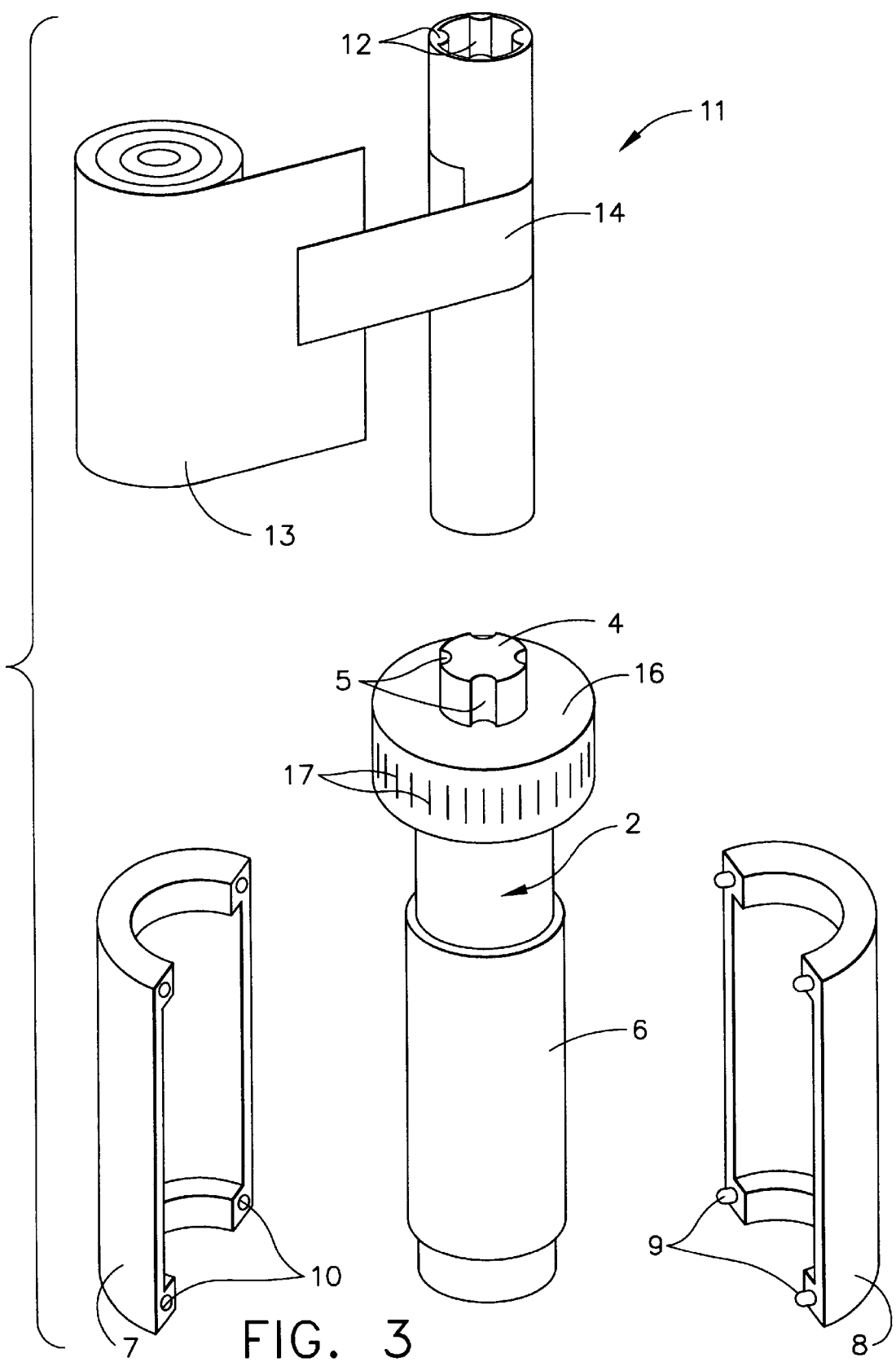
FIG. 3 shows a perspective drawing of the parts involved in the bandage applicator included in the present invention.

The applicator 1 of the present invention comprises a main cylindrical body 2, one of the ends of which is open whereas the other end has a cylindrical extension 4 fitted with certain longitudinal slots 5 around its periphery. The main body 2 has around it a projection 6 on which two identical and opposing half-casings 7, 8 are attached by means of grooving and tonguing when certain studs 9 are placed in certain opposing housings 10.

The half-casings provide a handle for the applicator allowing the main body 2 to turn. On the extension of the said body 2 a tubular portion 11 is attached by grooving and tonguing as it has certain longitudinal ridges 12 which fit into the slots 5, making the turning of the tubular part 11 and the main body 2 an interlocked movement.

The bandage 13 is rolled around the tubular part 11, attached to the same by means of an adhesive element 14 on one end, with the bandage having another adhesive element at the other end 15 to allow the beginning of the bandage to be found.

The tubular part 11 may be attached to the extension 4 by means of either of its two ends, thus favoring at all times the holding of the applicator in a more comfortable way for the better unwinding and turning of the bandage, by merely changing the end which is inserted as the bandage is applied.

The main body 2 has another projection 16 on its periphery, on the outside edge of which there are certain transverse linear ridges 17 to facilitate the braking, by means of the pressure of a finger, the rotating movement of the main body 2 as the bandage unwinds, in order to regulate the tension of the bandaging.

Having sufficiently described the nature of the invention, as well as the manner in which it may be implemented in practice, it must be noted for the record that the provisions indicated above and illustrated in the attached drawings are liable to modifications in detail insofar as the same do not change their fundamental principle.

What is claimed is:

1. A bandage applicator comprising:
   a main cylindrical body having a cylindrical extension on a top portion thereof, the cylindrical extension having a plurality of longitudinal slots on an outer portion thereof;
   a brake mechanism provided on the main cylindrical body for braking a rotational movement of the main cylindrical body, an outer portion of the brake mechanism including a plurality of transverse linear ridges for facilitating the braking of the rotational movement of the main cylindrical body when pressure is applied to the transverse linear ridges;
   a tubular part provided on the cylindrical extension of the main body, the tubular part having a plurality of inner longitudinal ridges that receive the longitudinal slots of the cylindrical extension for providing a secure connection between the tubular part and the main cylindrical body; and
   a handle portion disposed around a substantial portion of the main cylindrical body, the handle portion having a surface area that is greater than a surface area of the main cylindrical body for substantially limiting transfer of rotational movement from the main cylindrical body to the handle portion.

2. The bandage applicator of claim 1, wherein the tubular part further includes a bandage rolled around an outer portion of the tubular part.

3. The bandage applicator of claim 1, wherein the handle portion further comprises first and second housings disposed around the main cylindrical body, the first and second housings being attached to each other by studs in the first housing being received by openings and the second housing.

4. The bandage applicator of claim 1, wherein the braking mechanism has a eater than a diameter of the main cylindrical.

* * * * *